United States Patent
Ploetz et al.

[11] Patent Number: 5,828,722
[45] Date of Patent: Oct. 27, 1998

[54] X-RAY DIAGNOSTIC APPARATUS FOR TOMOSYNTHESIS HAVING A DETECTOR THAT DETECTS POSITIONAL RELATIONSHIPS

[75] Inventors: Josef Ploetz; Manfred Franetzki, both of Bensheim, Germany

[73] Assignee: Sirona Dental Systems GmbH & Co., KG, Paris, France

[21] Appl. No.: 856,147

[22] Filed: May 14, 1997

[30] Foreign Application Priority Data

May 17, 1996 [DE] Germany ............... 196 19 925.5

[51] Int. Cl.⁶ ..................................... A61B 6/03
[52] U.S. Cl. ...................... 378/38; 378/170; 378/205
[58] Field of Search .................. 378/38, 39, 21, 378/22, 25, 24, 23, 168, 170, 205, 204

[56] References Cited

U.S. PATENT DOCUMENTS

| | | |
|---|---|---|
| 4,211,927 | 7/1980 | Hellstrom et al. . |
| 4,907,251 | 3/1990 | Mork et al. . |
| 5,113,424 | 5/1992 | Burdea et al. ................ 378/205 X |
| 5,463,669 | 10/1995 | Kaplan .................... 378/205 |
| 5,598,454 | 1/1997 | Franetzki et al. . |
| 5,629,972 | 5/1997 | Hausmann et al. ........... 378/205 X |

FOREIGN PATENT DOCUMENTS

| | | |
|---|---|---|
| A-3808009 | 9/1988 | Germany . |
| A-4414689 | 11/1995 | Germany . |
| WO-A-9322893 | 11/1993 | WIPO . |

*Primary Examiner*—David P. Porta
*Attorney, Agent, or Firm*—Sughrue, Mion, Zinn, Macpeak & Seas, PLLC

[57] ABSTRACT

An diagnostic apparatus for generating X-ray exposures for tomosynthesis includes a position detector (2, 4) for registering the mutual positional relationship between the radiation transmitter (1) and/or the radiation receiver (3) and/or the object (7) under examination. The position detector (2, 4) can be arranged in part or in whole on the radiation transmitter (1), on the radiation receiver (3) or on the object (7) under examination. An evaluation device (11) evaluates the signals from the position detector (2, 4) and generates correction signals if the relative position between the radiation transmitter (1) and/or the radiation receiver (3) and/or the object (7) under examination deviates from the home position. The correction signals are then fed to an image-generating device (12) for use in the image processing.

17 Claims, 6 Drawing Sheets

X-RAY DIAGNOSTIC APPARATUS FOR TOMOSYNTHESIS HAVING A DETECTOR THAT DETECTS POSITIONAL RELATIONSHIPS

FIELD OF AND BACKGROUND OF THE INVENTION

The invention relates to new and useful improvements in X-ray diagnostic devices used for generating tomosynthesis recordings, such as tomographic images.

PCT patent publication WO 93/22 893 A1 discloses a method with which it is possible to reconstruct an exposure of an object under examination without knowledge of the projection angle $\alpha$ and without knowledge of the geometric arrangement of radiation transmitter, radiation receiver and focal plane. According to this method, a reference object made of radiation-absorbing material having a known size and known distance from the radiation receiver is provided in the region of the radiation receiver and is projected onto the radiation receiver during each individual projection. The geometric arrangement and the two-dimensional projection angle $\alpha$ can then be determined on the basis of the three-dimensional imaging of the reference object onto the radiation receiver for each individual projection. In the case disclosed, the reference object is arranged on a bite-wing holder which also carries the radiation receiver.

A holder for positioning a radiation transmitter of an X-ray diagnostic apparatus for tomosynthesis is known from German patent publication DE 44 14 689 A1. A carrying arm is coupled to the holder. As viewed in the radiation direction, a spherical reference object is arranged on the carrying arm in front of the object under examination. A radiation receiver is arranged behind the object under examination. The holder prescribes, first, the distance from the radiation sensor to the reference object and to the radiation receiver, and, second, the angle $\alpha$ of a bundle of radiation emitted by the radiation transmitter in relation to a reference axis of the holding device. It is further known to arrange the radiation source adjustably in a housing to which a positioning device for the reference object and the radiation receiver may be coupled.

In the case of tomosynthesis, the relative positions and locations of radiation transmitter, object under examination and radiation receiver must be known for all of the plurality of projections (irradiation angles). As already explained, according to WO 93/22 893 this is achieved by evaluating the image signals which are generated when the reference object, which is rigidly connected to the radiation receiver, is transilluminated. In this case, however, when the object under examination is transilluminated, undesired superimposition of the reference object onto the image signals results. Elaborate processing is then required to calculate out the superimposition caused by the reference object from the image signals.

According to DE 44 14 689 A1, the information which is necessary for reconstructing the exposure is prescribed as a result of the construction, that is to say as a result of the fixedly prescribed arrangement of radiation transmitter, object under examination and radiation receiver. Because of the greater outlay in terms of construction, the costs of such an X-ray diagnostic apparatus increase as a result. In addition, the object under examination must be rigidly fixed. In particular, human patients being examined find it highly unpleasant to be rigidly restrained.

OBJECTS OF THE INVENTION

In the case of both of the solution proposals described above, it is considered disadvantageous that changes in the positional relationship between the object being recorded and the radiation receiver cannot be detected or accommodated. Another drawback of these solutions is that such changes in relative location may have a detrimental effect on the images produced.

A first object of the invention is therefore, to provide an X-ray diagnostic apparatus including innovations beyond those exhibited by the apparatuses described above. It is a further object of the invention to render X-ray diagnostic apparatuses less susceptible to changes in position between the object to be recorded, the radiation receiver, etc.

SUMMARY OF THE INVENTION

These and other objects are achieved by the teachings of the independent claims. Particularly advantageous refinements of the invention are the subject matter of the dependent claims.

An X-ray diagnostic apparatus according to the invention is capable of generating a tomosynthesis recording and includes a radiation transmitter that transilluminates an object under examination from a plurality of different directions. A radiation receiver is adjustably mounted relative to the radiation transmitter and produces radiation signals for generating the tomosynthesis recording of an object under examination. An image-generating device in the apparatus receives the radiation signals for each of the plurality of different directions and computes the tomosynthesis recording of the object under examination. Further, at least one position detector is included, which produces position signals. The position signals describe an actual positional relationship between one or more of the radiation transmitter, the radiation receiver, and/or the object under examination. The position detector can be mounted on the radiation transmitter, the radiation receiver, or the object under examination or on any combination of these. An evaluation device in the apparatus evaluates the position signals to determine a deviation between the actual positional relationship and a predetermined, desired relationship. The evaluation device additionally generates correction signals in accordance with the evaluated deviation and outputs the correction signals to the image-generating device.

One advantage of the invention lies in the use of position detectors to register the relative location between the radiation transmitter, the radiation receiver and/or the object under examination. As a result, no mechanically rigid coupling has to be provided. Also, the need for a reference object that first has to be superimposed and then processed out is avoided.

According to preferred embodiments, either some form of coupling, or no coupling, can be provided between two or more of the radiation transmitter, the radiation receiver and the object under examination. Examples of couplings include a coupling device that limits the amount of permissible relative shift and an elastic coupling device. By providing such a coupling between the radiation transmitter, the radiation receiver, and/or the object under examination, the object under examination is permitted a certain freedom of movement. Particularly advantageous is a coupling in which a small restoring torque acts in the event of small deviations from a desired reference position and a large restoring torque acts in the event of large deviations.

According to the invention, correction signals are generated depending on the relationship between the radiation transmitter and/or the radiation receiver and/or the object under examination. Another preferred embodiment provides the further advantage that the radiation transmitter is stimulated to emit radiation only if prescribed limits on the correction signals are not exceeded. Yet another embodiment gives an indication, such as an audible or visible signal, if the correction signals exceed the prescribed limits. The invention thereby ensures that blur-free recordings are reliably obtained. This provides yet another related advantage, in that radiation stress resulting from repeated transilluminations of the object under examination, resulting from multiple attempts at obtaining satisfactory recordings, is significantly reduced.

BRIEF DESCRIPTION OF THE DRAWINGS

The invention and further advantageous refinements of the invention according to the features of the dependent claims are explained in more detail below with the aid of diagrammatic, exemplary embodiments in the drawing, in which:

DETAILED DESCRIPTION OF THE PREFERRED EMBODIMENTS

Figure 1:
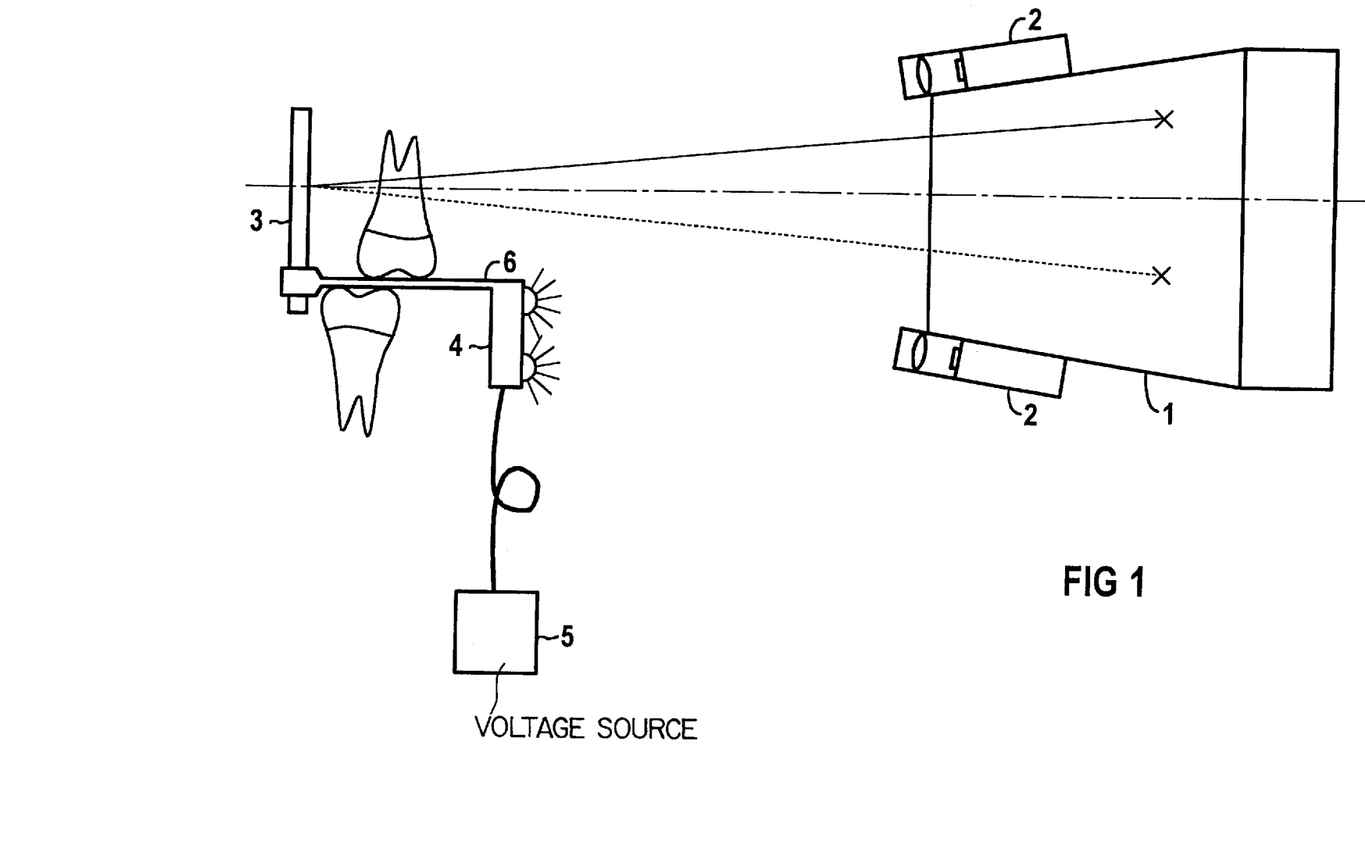
FIG. 1 shows an X-ray diagnostic apparatus for tomosynthesis according to one embodiment of the invention, in a basic illustration.

FIG. 1 illustrates one embodiment of an X-ray diagnostic apparatus for tomosynthesis. The apparatus has a radiation transmitter 1, to which, in this embodiment, the receiver 2 of a position detector is mounted. The radiation transmitter 1 is associated with a radiation receiver 3, which receives the radiation originating from the radiation transmitter 1. The transmitter 4 of the position detector is assigned to this radiation receiver 3. In the present embodiment, the transmitter 4 is implemented as an infrared transmitter, whose light is converted by the receiver 2 into electrical signals. These electrical signals are fed to an evaluation device 11 (see FIG. 2), which uses these electrical signals to determine the distance, the irradiation angle and the irradiation direction. The voltage from a voltage source 5 is supplied to the transmitter 4. In this embodiment, both the radiation receiver 3 and the transmitter 4 are arranged on a holder 6 implemented as a bite-wing holder.

While the above embodiment implements the position detector using an infrared transmitter and sensor, within the context of the invention, the position detector may be implemented in a wide variety of ways. Examples include magnetic, electromagnetic, optical, acoustic or mechanical devices. Furthermore, the arrangement for the position detector is also very versatile. Thus, e.g., contrary to the embodiment of FIG. 1, the transmitter 4 of the position detector can be assigned to the radiation transmitter 1 while the receiver 2 of the position detector is assigned to the radiation receiver 3. According to yet another configuration, the transmitter 4 and receiver 3 can, for example, both be provided on the radiation transmitter 1. This is accomplished, e.g., by having the transmitter 4 transmit a beam of radiation that is reflected by a reference point assigned to the radiation receiver 3 and having the reflected radiation be received by a receiver 2 that is also provided on the radiation transmitter 1.

As shown in FIG. 1, there need be no mechanical coupling between the radiation transmitter 1 and the radiation receiver 3. However, it is equally possible to provide a coupling for limiting the amount of positional change permitted. Another possibility is an elastic coupling which allows a certain clearance for the object under examination to move. It is particularly advantageous if the coupling is implemented in such a way that a small restoring force or torque is generated for small deviations from the norm, and a large restoring torque is generated for large deviations.

Figure 3:
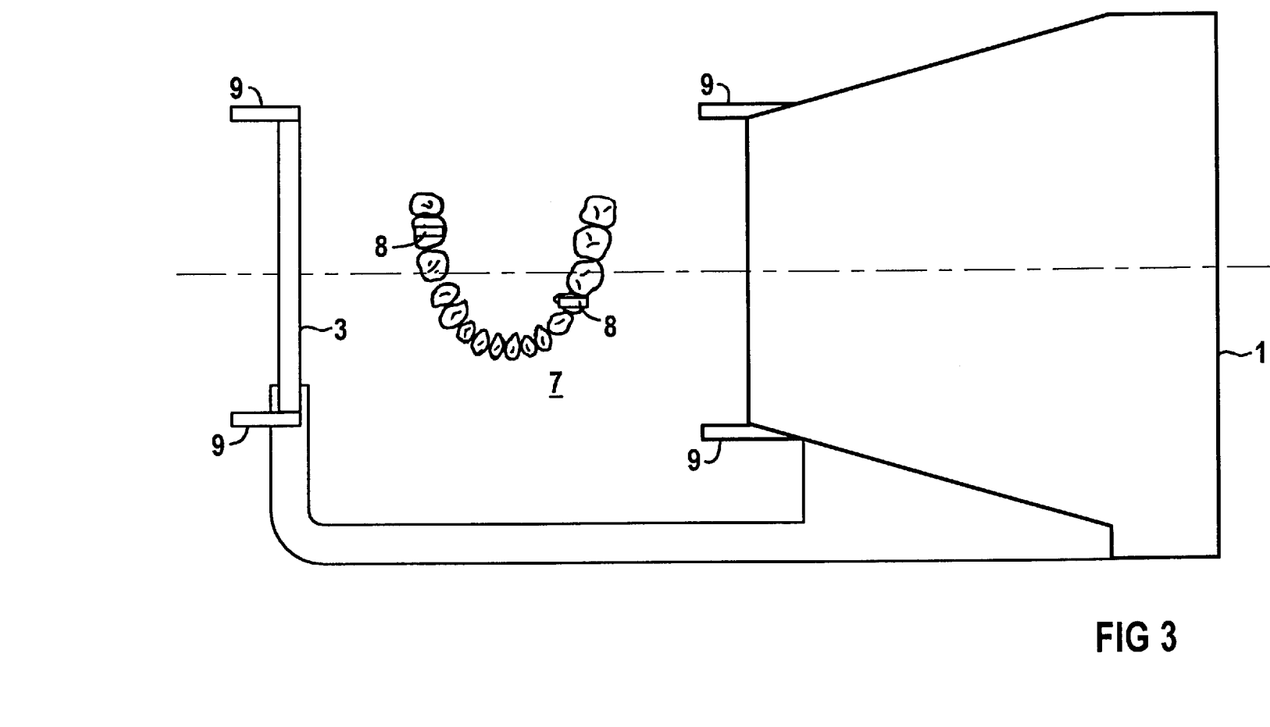
FIG. 3 shows an exemplary embodiment that detects the movement of an object under examination in relation to the radiation receiver.
Figure 4:
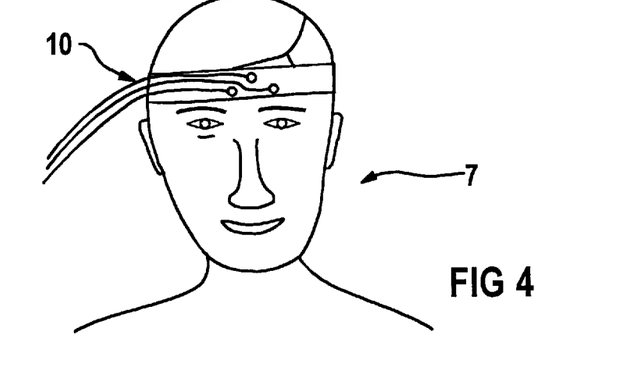
FIG. 4 shows a position detector arranged on the object under examination, FIG. 5 also shows a position detector arranged on the object under examination.
Figure 5:
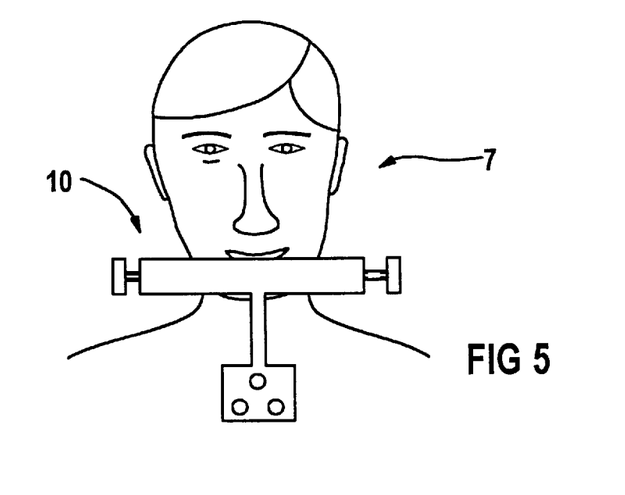
Figure 6:
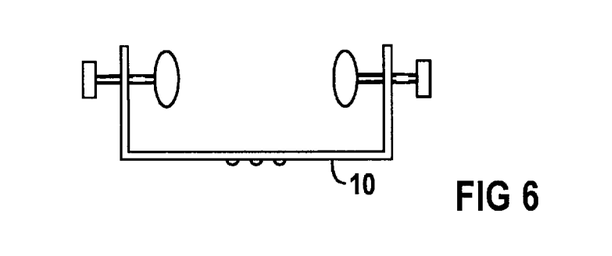
FIG. 6 shows a device having position detectors according to FIG. 5 in a plan view.

As evident from FIGS. 3, 4 and 5, the position detector need not have only a fixed relationship to the radiation transmitter 1, as is illustrated in FIG. 1, but can also be directly and immediately assigned to the object under examination. As shown in FIG. 3, the object 7 under examination, for example the jaw, is assigned the magnets 8, whose magnetic fields are received by magnetic field sensors 9. The magnetic field sensors 9, which can, e.g., be provided on the radiation receiver 3 and/or on the radiation transmitter 1, convert the magnetic fields into electrical signals which are then fed to the evaluation unit 11. An electromagnetic device in which either the magnetic fields are generated by coils or else are detected by means of coils can also be used, for instance, as the position detector. Use of changing magnetic fields allows the measurement to be decoupled from static interfering fields, whereby the precision of the measurement is improved.

The transmitter or receiver of the position detector can also be arranged on the object 7 under examination, for example on the head, and in particular on the forehead, as shown in FIG. 4. Alternatively, the position detector can be provided on a holding device 10 for the chin. By arranging the position detector at as great a distance as possible from the object 7 under examination, the measurement accuracy can be increased considerably, since when the object 7 under examination moves out of the rest position, a relatively large leverage, that is to say a relatively large deflection, results.

Figure 2:
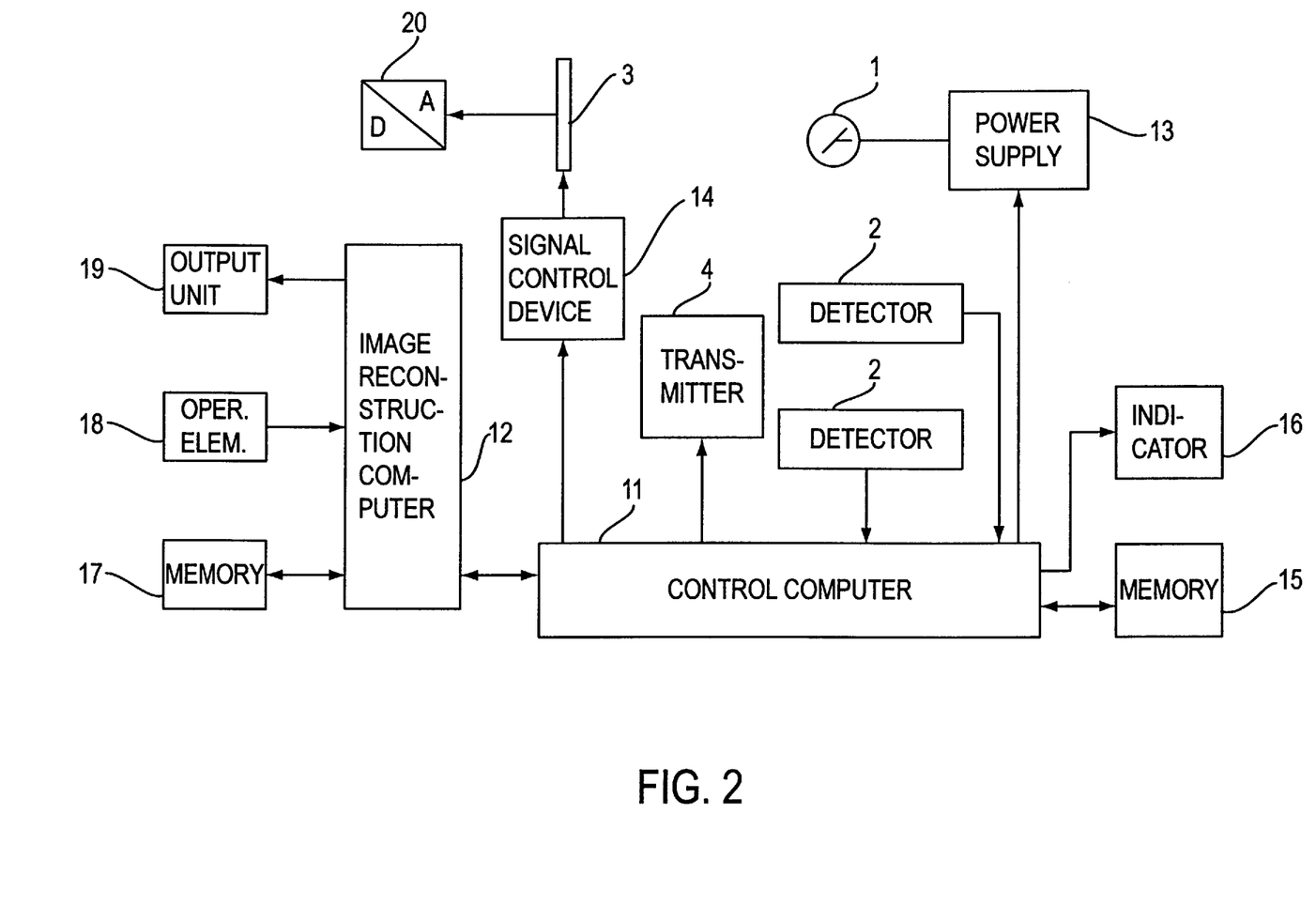
FIG. 2 shows a block diagram of an X-ray diagnostic apparatus according to another embodiment of the invention.

FIG. 2 shows a further preferred embodiment of an X-ray diagnostic apparatus according to the invention. In addition to the radiation transmitter 1, the position detector 2, 4 and the radiation receiver 3, the diagnostic apparatus includes a control computer 11 and an image reconstruction computer 12. The control computer 11 controls a power supply device 13 for the radiation transmitter 1, as well controlling the transmitter. 4 of the position detector and a signal control device 14 for the radiation receiver 3. The control computer 11 also has connections to the image reconstruction computer 12, to a memory 15 and to an indicator 16, and receives signals from the receiver 2 of the position detector. Associated with the image reconstruction computer 12 are a further memory 17, operating elements 18, an output unit 19 and an analog/digital converter 20 which converts the signals originating from the radiation receiver 3.

As already explained, the control computer 11 calculates the distance of the radiation transmitter 1 from the radiation receiver 3, the irradiation angle and the irradiation direction based on the signals supplied by the position detector 2, 4. If the alignment of the radiation transmitter 1, the object 7 under examination and the radiation receiver 3 deviates from a desired relationship, then the control computer 11 forms correction signals which are fed to the image reconstruction computer 12, either immediately or at a later time after temporary storage in the memory 15. These correction signals are then taken into account during the calculation of a transillumination image of the object 7 under examination.

According to an advantageous embodiment, depending on the correction signals, the radiation transmitter 1 can be stimulated to emit radiation only if predetermined limits on the correction signals are not exceeded. Either in addition or as an alternative, an indicator 16 can be provided for indicating, for example, that no blur-free recording can be generated because of the movement of the object 7 under examination. The indicator 16 can be, for example, a speaker, an LED, or a display for generating an audible and/or a visible signal.

Figure 8:
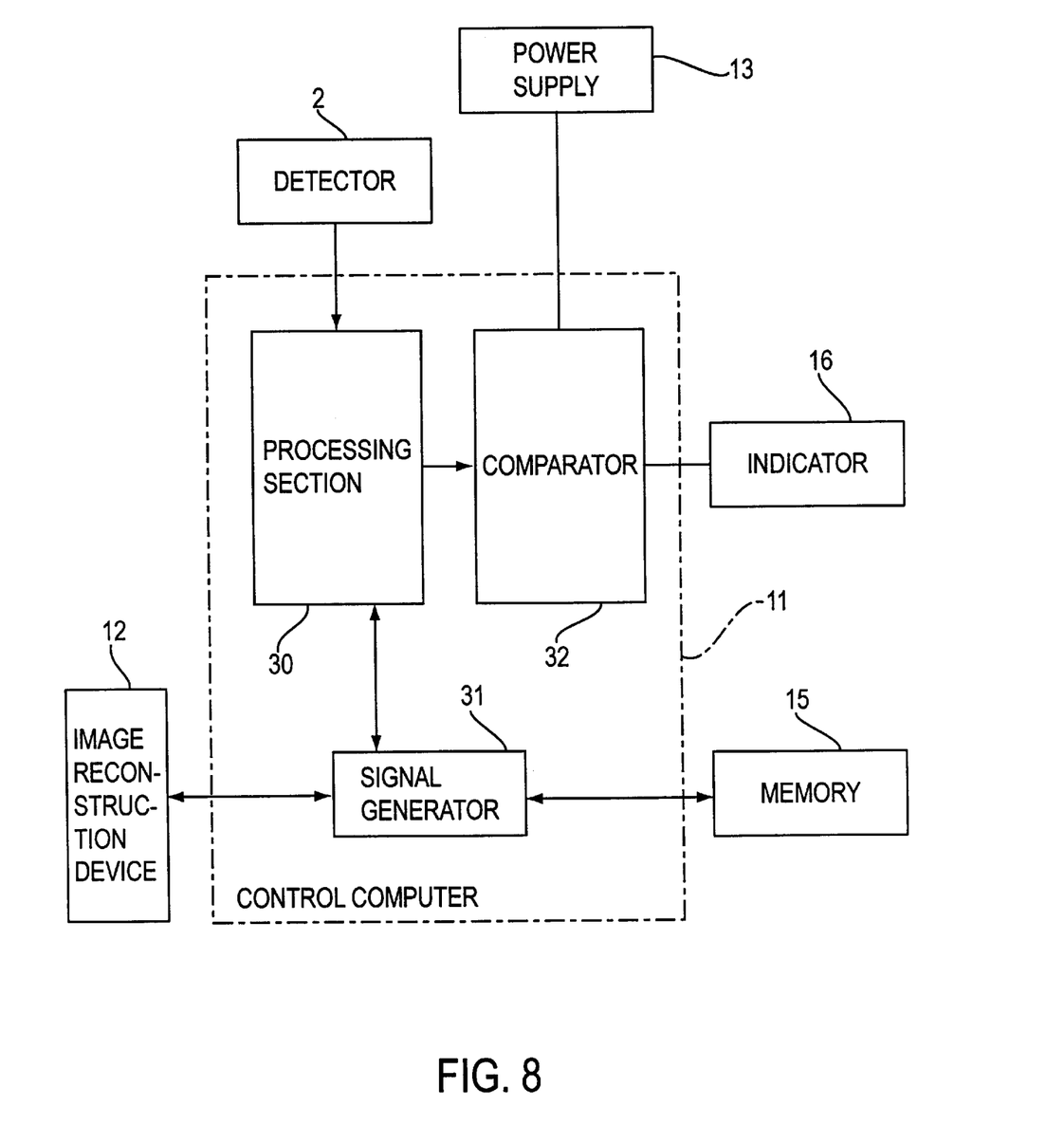
FIG. 8 is a functional block diagram illustrating an internal operation of a control computer of the X-ray diagnostic apparatus.

FIG. 8 is a functional block diagram for illustrating internal operational features of the control computer 11 according to one embodiment of the invention. As shown, the control computer 11 includes a processing section 30, a signal generator 31 and a comparator 32. The processing section, inter alia, receives position signals from the receiver 2 of the position detector. These position signals are indicative of actual positional relationships between the transmitter 4 and the receiver 2 of the position detector. Based on the position signals received, the processing section 30 calculates the amount of deviation between the actual, momentary positional relationship and a pre-set, desired relationship, e.g., in the manner described above. This calculation yields an evaluation result, which is forwarded to the signal generator 31 and to the comparator 32.

The signal generator 31 generates the correction signals described above based on the evaluation result received from the processing section 30. These correction signals are then output to the image reconstruction computer 12 or to the memory 15 as needed.

The comparator 32 uses the evaluation result to compare whether the amount of deviation between the actual, momentary positional relationship and a pre-set, desired relationship is within a prescribed, predetermined limit. If the evaluation result exceeds the prescribed limit, this indicates that the deviation is sufficiently large that, even with the use of the correction signals, the reconstruction computer 12 will not be capable of constructing satisfactory images. Accordingly, if the comparator 32 determines that the prescribed limit has been exceeded, the comparator will output a signal preventing the power supply device 13 from stimulating the radiation transmitter 1 to emit radiation. On the other hand, if the comparator 32 determines that the deviation is within the prescribed limit, the comparator's output will provide an enabling signal to the power supply device 13. The output from the comparator 32 can additionally or alternatively be used to actuate the indicator 16, e.g., in the manner described previously.

In the case of a conventional panoramic X-ray apparatus for generating tomograms, the object 7 under examination is normally fixed as rigidly as possible on the X-ray apparatus by means of bite-wing holders, frontal supports or earpieces. This is unpleasant for the person being examined. On the other hand, also conventionally, movements of the object 7 under examination lead to a disturbance in the X-ray picture generated, which is also undesirable. According to the invention, it is possible, as already explained, to give the object 7 under examination a certain freedom of movement. This is accomplished by registering the object's exact position and spatial orientation along with its change in position during the recording sequence, through measurement by means of a position detector.

Correction signals are then formed in the control computer 11 from the signals output by the position detector. The correction signals are then used, before carrying out the tomographic merging process, to assign the correct image contents to the object details from the particular image layer that is desired to be imaged sharply, and to track the location of the desired image layer to the patient's movement. As a precondition, the resulting image signals, which change continuously corresponding to the tomographic scanning movement of the X-ray apparatus, must be registered in fine steps and initially stored. It is also necessary to postpone preparing the computerized merging for the tomogram that is desired for a given object region until the complete image signals relating to that object region are available.

The correction signals which are generated from the position signals influence several of the image reconstruction parameters. These parameters include the derivation intervals for the individual images/individual image signals as well as the displacement of the individual images/image signals parallel and orthogonal to the tomographic scanning direction. The correction signals also contain rotations of the individual images/image signals as well as changes, differentiated with respect to direction and position, of the magnification of the individual images/image signals, and the combining of effective individual images/individual image signals from a plurality of image strips/image signal strips according to derivation intervals which vary in the direction orthogonal to the tomographic scanning direction.

Figure 7:
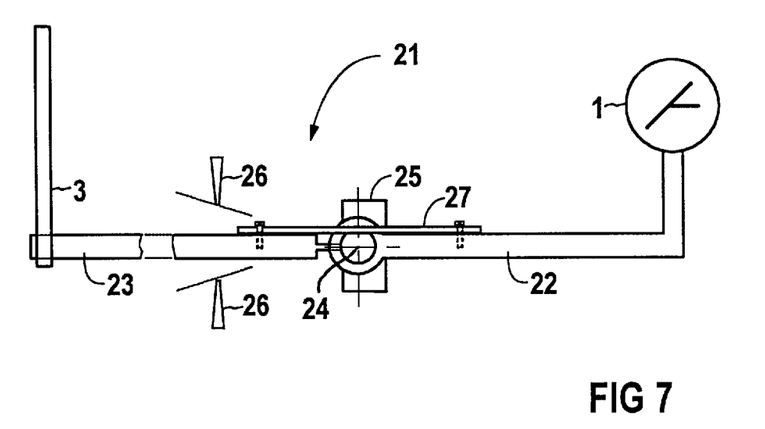
FIG. 7 shows a coupling device of the X-ray diagnostic apparatus according to FIG. 1.

FIG. 7 illustrates a basic coupling device 21 that limits or elastically couples the amount of permissible relative adjustment between the radiation transmitter 1 and the radiation receiver 3 or the object 7 under examination. In an alternative embodiment, the device 21 could be provided between the radiation receiver 3 and the object 7 under examination. The coupling device 21 illustrated in FIG. 7 has a first arm 22 which is connected to the radiation transmitter 1. The radiation receiver 3 is arranged on a second arm 23 of the coupling device 21. The object under examination, which is not shown in FIG. 7, is usually arranged in the region of the radiation receiver 3. The first and second arms 22, 23 are mounted such that they are pivotable about an axis of rotation 24. A distance pick-up 25 may be provided for detecting the pivoting of the arms 22, 23. Rotary encoders or strain gauges, for example, are suitable as distance pick-ups 25. Assigned to the coupling device 21 are two distance limiters 26 which, in the present embodiment, limit the adjustability of the second arm 23.

If a spring element 27, for example a leaf spring, is connected to the arms 22, 23, then elastic adjustment of the arms 22, 23 relative to each other and about the axis of rotation 24 is provided. The spring element 27 can advantageously be implemented to produce a small restoring torque in the event of a small deviation from the desired mutual positional relationship between the radiation transmitter 1 and the radiation receiver 3. On the other hand, a large restoring torque is produced in response to a large deviation. The signals generated by the distance pick-up 25 are fed to the evaluation device 11, as already explained. Within the context of the invention, the arms 22, 23 may also be further adjustable about an axis at right angles to the axis of rotation 24, or in other spacial directions via a universal rotary joint.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. An X-ray diagnostic apparatus for generating a tomosynthesis recording, comprising:
    a radiation transmitter that transilluminates an object under examination from a plurality of different directions;
    a radiation receiver that is adjustably mounted relative to said radiation transmitter and that produces radiation signals for generating the tomosynthesis recording of the object under examination;
    an image-generating device that receives the radiation signals for each of the plurality of different directions and computes the tomosynthesis recording of the object under examination;
    at least one position detector that produces position signals in accordance with a positional relationship between at least any two of (i) said radiation transmitter, (ii) said radiation receiver, and (iii) the object under examination, wherein said position detector is mounted on at least any one of said radiation transmitter, said radiation receiver, or the object under examination; and
    an evaluation device that (i) evaluates the position signals to determine a deviation between the positional relationship and a desired relationship, (ii) generates correction signals in accordance with the evaluated deviation, and (iii) outputs the correction signals to said image-generating device.

2. The X-ray diagnostic apparatus as claimed in claim 1, wherein said image-generating device computes the tomosynthesis recording of the object under examination on the basis of at least the radiation signals and the correction signals.

3. The X-ray diagnostic apparatus as claimed in claim 1, wherein:
    said position detector is implemented as at least any one of a magnetic, electromagnetic, optical, acoustic or mechanical device;
    said position detector comprises a transmitter and a receiver;
    said transmitter of said position detector is mounted on at least one of said radiation receiver or the object under examination; and
    said receiver of said position detector is arranged on said radiation transmitter.

4. The X-ray diagnostic apparatus as claimed in claim 1, wherein:
    said position detector is implemented as at least any one of a magnetic, electromagnetic, optical, acoustic or mechanical device;
    said position detector comprises a transmitter and a receiver;
    said transmitter of said position detector is arranged on said radiation transmitter; and
    said receiver of said position detector is mounted on at least one of said radiation receiver or the object under examination.

5. The X-ray diagnostic apparatus as claimed in claim 1, further comprising:
    a holding device for holding the object to be examined; wherein:
        said position detector is implemented as at least any one of a magnetic, electromagnetic, optical, acoustic or mechanical device;
        said position detector comprises a transmitter and a receiver;
        said transmitter of said position detector is mounted on said holding device; and
        said receiver of said position detector is arranged on said radiation transmitter.

6. The X-ray diagnostic apparatus as claimed in claim 1, further comprising:
    a holding device for holding the object to be examined; wherein:
        said position detector is implemented as at least any one of a magnetic, electromagnetic, optical, acoustic or mechanical device;
        said position detector comprises a transmitter and a receiver;
        said transmitter of said position detector is arranged on said radiation transmitter; and
        said receiver of said position detector is mounted on said holding device.

7. The X-ray diagnostic apparatus as claimed in claim 1, further comprising:
    a coupling between said radiation transmitter and a coupled object, the coupled object including at least one of said radiation receiver and the object under examination, wherein said coupling limits a relative displacement between said radiation transmitter and the coupled object.

8. The X-ray diagnostic apparatus as claimed in claim 7, wherein said coupling is an elastic coupling that exhibits a restoring force substantially proportional to the deviation from the desired relationship.

9. The X-ray diagnostic apparatus as claimed in claim 7, wherein said coupling is an elastic coupling that exhibits a small restoring torque in response to a small deviation from the desired relationship and exhibits a large restoring torque in response to a large deviation from the desired relationship.

10. The X-ray diagnostic apparatus as claimed in claim 1, wherein said evaluation device (iv) evaluates whether or not the correction signals exceed prescribed limits.

11. The X-ray diagnostic apparatus as claimed in claim 10, wherein, if the correction signals are within the prescribed limits, said evaluation device (v) enables said radiation transmitter to be stimulated to emit radiation.

12. The X-ray diagnostic apparatus as claimed in claim 10, further comprising:
    an indicator connected to said evaluation device for providing an indication if the correction signals exceed the prescribed limits.

13. The X-ray diagnostic apparatus as claimed in claim 1, wherein said evaluation device comprises:
    a processor that evaluates, from the position signals received from said position detector, a deviation between the positional relationship and the desired relationship, and produces an evaluation result;

a signal generator that generates the correction signals based on the evaluation result.

14. The X-ray diagnostic apparatus as claimed in claim 13, wherein said evaluation device further comprises:

a comparator that determines whether the deviation is within a prescribed limit, and that produces a comparison result.

15. The X-ray diagnostic apparatus as claimed in claim 14, further comprising:

an actuator controlled by the comparison result of said comparator to stimulate said radiation transmitter to emit radiation only if the deviation lies within the prescribed limit.

16. The X-ray diagnostic apparatus as claimed in claim 14, further comprising:

an indicator controlled by the comparison result of said comparator to output a signal if the deviation exceeds the prescribed limit.

17. An X-ray diagnostic apparatus for tomosynthesis, comprising:

a radiation transmitter and a radiation receiver provided for generating tomosynthesis recordings of an object under examination, said radiation transmitter and said radiation receiver being adjustably mounted such that, when the object under examination is transilluminated from different directions, signals are derived at said radiation receiver for each of the directions;

an image-generating device receiving the signals in order to calculate a tomosynthesis recording of the object under examination;

at least one position detector provided for registering, as position signals, a positional relationship between at least one of (i) said radiation transmitter and said radiation receiver, (ii) said radiation transmitter and the object under examination, and (iii) said radiation receiver and the object under examination, said position detector being arranged on at least one of said radiation transmitter, said radiation receiver, and the object under examination; and an evaluation device provided for evaluating the position signals from said position detector, and for generating correction signals if the positional relationship deviates from a desired relationship;

whereby the correction signals are supplied from said evaluation device to said image-generating device.

* * * * *